(12) United States Patent
Shaffermann

(10) Patent No.: US 6,248,574 B1
(45) Date of Patent: Jun. 19, 2001

(54) POLYPEPTIDES SELECTIVELY REACTIVE WITH ANTIBODIES AGAINST HUMAN IMMUNODEFICIENCY VIRUS AND VACCINES COMPRISING THE POLYPEPTIDES

(76) Inventor: Avigdor Shaffermann, 69 Ben Gurion Street, Ness-Ziona 70450 (IL)

( * ) Notice: Subject to any disclaimer, the term of this patent is extended or adjusted under 35 U.S.C. 154(b) by 0 days.

(21) Appl. No.: 07/450,150

(22) Filed: Dec. 13, 1989

(51) Int. Cl.[7] .............................. C12N 9/00; C12N 9/38; C07K 1/00; C12Q 1/70

(52) U.S. Cl. .............................. 435/183; 435/207; 435/5; 435/974; 424/89; 530/326; 530/350; 530/395; 530/403; 930/221

(58) Field of Search ................................. 435/5, 183, 207, 435/974, 188; 424/89, 192.1, 194.11, 261.1; 530/326, 350, 395, 403, 389.4; 930/221

(56) References Cited

U.S. PATENT DOCUMENTS

| | | | |
|---|---|---|---|
| 4,736,896 | 4/1988 | Wang et al. | 435/5 |
| 4,745,055 | * 5/1988 | Schenk et al. | 435/7 |
| 4,918,166 | * 4/1990 | Kingsman | 530/350 |

FOREIGN PATENT DOCUMENTS

| | | | |
|---|---|---|---|
| 8606414 | * 6/1986 | (EP) | . |
| 0214709 | 3/1987 | (EP) | . |
| 0227169 | 7/1987 | (EP) | . |
| 231914 | 8/1987 | (EP) | . |
| 0251612 | 1/1988 | (EP) | . |
| 20283327 | * 1/1988 | (EP) | . |
| 278148 | 8/1988 | (EP) | . |
| 0305777 | 3/1989 | (EP) | . |
| 0330359 | 8/1989 | (EP) | . |
| 0335134 | 10/1989 | (EP) | . |
| 0362909 | 4/1990 | (EP) | . |
| WO 8602383 | 4/1986 | (WO) | . |
| WO 8606414 | 11/1986 | (WO) | . |
| WO 8706005 | 10/1987 | (WO) | . |
| WO 8800471 | 1/1988 | (WO) | . |
| WO8808005 | * 4/1988 | (WO) | . |
| WO 8808005 | 10/1988 | (WO) | . |
| WO 8909393 | 10/1988 | (WO) | . |
| WO 89/01494 | 2/1989 | (WO) | . |
| WO 8903844 | 5/1989 | (WO) | . |

OTHER PUBLICATIONS

P. Hilts, "Tests of a Vaccine on Monkeys Offer New Hope in AIDS Fight", *The New York Times,* vol. CXXXXIX No. 48,078, Dec., 1989.

M. Murphey–Corb, et al., "A Formalin–Inactivated Whole SIV Vaccine Confers Protection in Macaques", *Reports,* Dec., 1989, pp. 1293–1297.

"Isolation of a T–Lymphotropic Retrovirus from a Patient at Risk for Acquired Immune Deficiency Syndrome (AIDS)", *Science,* vol. 220, Apr. 1983, pp. 868–871.

D.D. Ho, et al., "Second Conserved Domain of gp120 is Important for HIV Infectivity and Antibody Neutralization", *Reports,* Feb., 1988, pp. 1021–1023.

A. Shaffeman, et al., "Patterns of Antibody Recognition of Selected Conserved Amino Acid Sequences from the HIV Envelope in Sera from Different States of HIV Infection", *AIDS Research and Human Retroviruses,* vol. 5, No. 1, 1989, pp. 33–39.

R. Gallo, et al., "Frequent Detection and Isolation of Cytopathic Retroviruses (HTLV–III) from Patients with AIDS and at Risk for AIDS", *Science* 224: 500–03 (1984).

M. Robert–Guroff, et al., "HTLV–III–Neutralizing Antibodies in Patients with AIDS and AIDS–Related Complex", *Nature,* 316: 72–74 (1985).

R.A. Weiss, et al., "Neutralization of Human T–Lymphotropic Virus Type III by Sera of AIDS and AIDS–Risk Patients", *Nature,* 316: 69–71 (1985).

G. Francini, et al., "Sequence of Simian Immunodeficiency Virus and its Relationship to the Human Immunodeficiency Viruses", *Nature,* 328: 539–42 (1987).

D.D. Ho, et al., "Human Immunodeficiency Virus Neutralizing Antibodies Recognize Several Conserved Domains on the Envelop Glycoprotiens", *Journal of Virology,* 61: 2024–28 (1987).

David D. Ho, et alii, "Human Immunodeficiency Virus Neutralizing Antibodies Reecognize Several Conserved Domains on the Envelope Glycoproteins," *Journal of Virology,* vol. 61, No. 6, issued Jun. 1987, pp. 2024–2028.*

Berzofsky, et al. *Immunochemistry,* vol. 110, 1989, abstract #110:17167s.*

Leny, et al., Klin Wochenschr (1987) 68:1042–1047.*

Rosen, et al., *HIV Detection by Genetic Engineering Methods,* 1989.*

Shafferman et al., "Patterns of antibody recognition of selected conserved amino acid sequences from the HIV envelope in sera from different stages of HIV infection", AIDS Res. Hum. Retro. 1989, 5 (1), 33–39.

Lenz et al., "Serologic AIDS diagnosis with polypeptides obtained by genetic technics of the human immunodeficiency virus (HIV–1) A", Klin Wochensohr, Nov. 2, 1987, 68(21), 1042–1047.

Bolognesi, "HIV antibodies and vaccine design", AIDS, vol. 3, 1989.

(List continued on next page.)

*Primary Examiner*—W. Gary Jones
*Assistant Examiner*—Bradley L. Sisson
(74) *Attorney, Agent, or Firm*—Elizabeth Arwine; John Francis Moran

(57) ABSTRACT

Highly conserved polypeptide sequences derived from gp41 and gp120, preferably from eleven to twenty-one amino acids in length, are joined (for example, via DNA recombinant techniques) to a non-HIV protein or polypeptide sequence comprising an amino-acid sequence not naturally encoded by the HIV genome, thereby forming a fusion protein. Such fusion proteins possess attributes that make them suitable for use in the diagnosis, treatment and prevention of HIV infection.

13 Claims, 4 Drawing Sheets

OTHER PUBLICATIONS

Chemical Abstracts, vol. 110, No. 19, May 8, 1989, abstract 171673r.

Ruegg et al., "Inhibition of lymphoproliferation by a synthetic peptide with sequence identity to gp41 of human immunodeficiency virus type 1", Chem. Abs., vol. 111, No. 15, Oct. 9, 1989, abstract 132340f.

Palker et al., "A conserved region at the carboxy terminus of human immunodeficiency virus gp 120 envelope protein contains an immunodominant epitope", Chem. Abst., vol. 107, No. 55, Aug. 3, 1987, abstract 37664y.

Hunt et al., "Mouse monoclonal antibody 5–21–3 recognizes a contiguous, conformation–dependent epitope and maps to a hydrophilic region in HIV–1 gp41", Chem. Abstr., vol. 113, No. 21, Nov. 19, 1990, abst. 189272f.

Gnann, Jr. et al., Chemical Abstracts, vol. 107, No. 25, Dec. 21, 1987, abstract 234358c, & J. Infect. Dis. 1987, 156 (2), pp. 261–267.

Shofirman et al., *AIDS Research and Human Retroviruses,* vol. 5, No. 1, 1989.*

J. I. Rosen, et al., "Immunoreactivity of AIDS/ARC Patient Sera With Synthetic Oligopeptides From HIV gp41", 1989, pp. 143–160.

* cited by examiner

FIGURE 1A

HIV88

HindIII

|  | Asn | Val | Thr | Glu | Asn | Phe | Asn | Met | Trp |
|---|---|---|---|---|---|---|---|---|---|
| AGCTT5 | AAC | GTA | ACT | GAA | AAC | TTC | AAC | ATG | TGG |
| A | TTG | CAT | TGA | CTT | TTG | AAG | TTG | TAC | ACC |

| Lys | Asn |  |
|---|---|---|
| AAA | AAC | CTGCA |
| TTT | 10TTG | G |

PstI

FIGURE 1B

HIV500

HindIII

|  | 15 | Lys | Ala | Lys | Arg | Arg | Val | Val | Gln | Arg |
|---|---|---|---|---|---|---|---|---|---|---|
| AGCTT |  | AAA | GCT | AAA | CGT | CGT | GTA | GTA | CAG | CGT |
| A |  | TTT | CGA | TTT | GCA | GCA | CAT | CAT | GTC | GCA |

| Glu | Lys | Arg | Ala | Val | Gly |  |
|---|---|---|---|---|---|---|
| GAA | 20AAG | CGC | GCT | GTA | GGT | CTGCA |
| CTT | TTC | GCG | CGA | CAT | CCA | G |

PstI

FIGURE 1C

HIV582

NcoI

|  | Glu | Arg | Tyr | Leu | Lys | Asp | Gln | Ala |
|---|---|---|---|---|---|---|---|---|
| CATG 5 | GAA | CGT | TAC | CTG | AAA | GAC | CAG | CAG |
|  | CTT | GCA | ATG | GAC | TTT | CTG | GTC | GTC |

| Leu | Leu | Gly | Ile | Trp | Gly | Cys | Ser | Gly | Lys |
|---|---|---|---|---|---|---|---|---|---|
| CTG | CTG | GGT | ATC | TGG | GGT | TGT | TCT | GGT | AAA |
| GAC | 10GAC | CCA | TAG | ACC | CCA | ACA | AGA | CCA | TTT |

| Leu | Ile | Cys |  |
|---|---|---|---|
| CTG | ATC | TGC | A |
| GAC | TAG | ACG | TTCGA |
|  | 15 |  | HindIII |

FIGURE 1D

HIV647

NcoI

|  | Glu | Glu | Ser | Gln | Asn | Gln | Gln | Glu | Lys |
|---|---|---|---|---|---|---|---|---|---|
| CATG20 | GAA | GAA | TCT | CAG | AAC | CAG | CAG | GAA | AAA |
|  | CTT | CTT | AGA | GTC | TTG | GTC | GTC | CTT | TTT |

| Asn | Glu | Gln | Glu | Leu | Leu | Glu | Leu | Asp | Lys |
|---|---|---|---|---|---|---|---|---|---|
| AAC | GAA | CAG | GAA | CTT | CTG | GAG | CTC | GAC | AAA |
| TTG | CTT | GTC | CTT | GAA | GAC | CTC | GAG | CTG | TTT |
|  | 25 |  |  |  |  |  |  |  |  |

| Trp | Ala |  |
|---|---|---|
| TGG | GCT | A |
| ACC | CGA | TTCGA |
|  |  | HindIII |

FIGURE 2A

SIV88

HindIII

|        | Asn | Val | Thr | Glu | Ser | Phe | Asp | Ala |
|--------|-----|-----|-----|-----|-----|-----|-----|-----|
| AGCTT5 | AAC | GTA | ACT | GAA | TCT | TTC | GAC | GCT |
| A      | TTG | CAT | TGA | CTT | AGA | AAG | CTG | CGA |

| Trp | Glu | Asn |       |
|-----|-----|-----|-------|
| TGG | GAA | AAC | CTGCA |
| ACC | CTT | TTG | G     |
|     | 10  |     | PstI  |

FIGURE 2B

SIV500

HindIII

|        | Arg | Tyr | Thr | Thr | Gly | Gly | Thr | Ser |
|--------|-----|-----|-----|-----|-----|-----|-----|-----|
| AGCTT5 | CGT | TAC | ACT | ACT | GGT | GGT | ACT | TCT |
| A      | GCA | ATG | TGA | TGA | CCA | CCA | TGA | AGA |

| Arg | Asn    | Lys | Arg |       |
|-----|--------|-----|-----|-------|
| CGT | AAC    | AAA | CGT | CTGCA |
| GCA | 20TTG  | TTT | GCA | G     |
|     |        |     | PstI |      |

FIGURE 2C

SIV582

NcoI

| | Glu | Lys | Tyr | Leu | Glu | Asp | Gln | Ala | |
|---|---|---|---|---|---|---|---|---|---|
| CATG 5 | GAA | AAG | TAC | CTG | GAA | GAC | CAG | GCT | |
| | CTT | TTC | ATG | GAC | CTT | CTG | GTC | CGA | |

| Gln | Leu | Asn | Ala | Trp | Gly | Cys | Ala | Phe | Arg |
|---|---|---|---|---|---|---|---|---|---|
| CAG | CTG | AAC | GCT | TGG | GGT | TGC | GCT | TTC | CGT |
| GTC | GAC | TTG | CGA | ACC | CCA | ACG | CGA | AAG | GCA |

| Gln | 10Val | Cys | |
|---|---|---|---|
| CAG | GTT | TGT | A |
| GTC | CAA | ACA | TTCGA |

Hind III

FIGURE 2D

SIV643

NcoI

| | Glu | Glu | Ala | Gln | Ile | Gln | Gln | Glu |
|---|---|---|---|---|---|---|---|---|
| CATG | GAA | GAA | GCT | CAG | ATC | CAG | CAG | GAA |
| | CTT | CTT | CGA | GTC | TAG | GTC | GTC | CTT |

| Lys | 20Asn | Met | Tyr | Glu | Leu | Gln | Lys | Leu | Asn |
|---|---|---|---|---|---|---|---|---|---|
| AAG | AAC | ATG | TAC | GAA | CTG | CAG | AAA | CTG | AAC |
| TTC | TTG | TAC | ATG | CTT | GAC | GTC | TTT | GAC | TTG |

| Ser | Trp | Asp | |
|---|---|---|---|
| AGC | TGG | GAC | A |
| TCG | 25ACC | CTG | TTCGA |

HindIII

POLYPEPTIDES SELECTIVELY REACTIVE WITH ANTIBODIES AGAINST HUMAN IMMUNODEFICIENCY VIRUS AND VACCINES COMPRISING THE POLYPEPTIDES

BACKGROUND OF THE INVENTION

This invention was made in part with U.S. Government Support under Contract No. DAMD17-87-C-7156 awarded by the United States Army Medical Research and Development Command to the National Research Council. The U.S. Government has certain rights in this invention.

The present invention relates to the production and use, in diagnosis, treatment and prevention of HIV infection, of an antigenic protein that reacts specifically with antibodies against the Human Immunodeficiency Virus type 1 (HIV-1). The present invention also relates to a self-replicating cell that produces such a recombinant protein; to a vaccine comprising the recombinant protein; to an antigen-based screening test, based on the protein, for detecting antibodies to HIV; to monoclonal and polyclonal antibodies, produced using the protein, that protect against HIV-1 infection or disease; and to an antibody-based screening test.

HIV has been established as the primary etiologic agent in pathogenesis of acquired immunodeficiency syndrome (AIDS) and related disorders. See, e.g., Gruest, J., et al., *Science* 220: 863–71 (1983); Gallo, R. C., et al., *Science* 224: 500–03 (1984). Because AIDS can be transmitted by blood products, a highly accurate method of screening blood samples for presence of the virus is desirable. Infection of humans with HIV leads to production of antibodies directed against most of the viral structural antigens, forming the basis for screening via viral lysate based tests. However, these tests have several disadvantages, including false positives thought to arise from the presence of non-viral proteins in the viral lysate preparations used in the solid phase component of the current assays.

The antibodies produced upon infection include antibodies against both core and envelope proteins. The emergence of antibodies to envelope glycoproteins, e.g., gp160, and its subunits gp120 (the extracellular glycoprotein or EGP) and gp41 (the transmembrane protein or TMP), appears to precede the emergence of antibodies to core proteins, leading researchers to study these proteins as a possible basis for improved diagnostic assays. In addition, these antibodies to env proteins appear to be involved in induction of active immunity, suggesting their use in vaccine preparation.

Based on study of the envelope amino acid sequences, and in an attempt to reduce the rate of false positives, the art has proposed serological assays employing synthetic polypeptides that mimic naturally occurring antigenic determinants on viral proteins. Data generated in studies using synthetic peptides have indicated that some of the conserved domains in gp120 and gp41, respectively, contain immunodominant epitopes that may be appropriate for diagnosis. From analysis of conserved HIV domains from gp41 it appears that, within a linear sequence spanning about 40 amino acids (amino acid 570–612), numerous and highly immunodominant epitopes of HIV reside. Wang, J. J. G., et al., *Proc. Nat'l Acad. Sci.* USA 83: 6159–63 (1986); Gnann, J. W., et al., *J. Infect. Dis.* 156: 261–67 (1987).

Conserved domains in gp120 and gp41 have also been identified that are involved in neutralization of different HIV isolates. Ho, D. D., et al., *J. Virol.* 61: 2024–28 (1987); *Science* 239: 1021–23 (1988). Neutralizing-specific antibodies to the major envelope glycoprotein are type-specific and have recently been mapped to a highly variable sequence of gp120. Putney, S. D., et al., *J. Cell. Biochem.* 12B: 5 (1988). Neutralization assays with immune sera from animals or humans, see Robert-Guroff, M., et al., *Nature* 316: 72–74 (1985); Weiss, R. A., et al., *Nature* 316: 69–71 (1985); Rasheed, S., et al., *Virology* 150: 1–6 (1986), have revealed that the envelope proteins contains epitopes that elicit antibodies capable of neutralizing HIV in vitro. But the presence of these antibodies in vivo has only a limited effect on progression of the disease, Robert-Guroff, M., et al., loc. cit.; Wendler, I., et al., *AIDS Res. Human Retroviruses* 3: 157–63 (1987), and no significant difference in titers which can be correlated with clinical status. In humans, there are no known patterns of antibody response indicative of immunity.

SUMMARY OF THE INVENTION

It is therefore an object of the present invention to provide a fusion protein, readily produced in commercially significant quantities, that is an effective vaccine for prevention of HIV infection.

It is a further object of the present invention to provide a fusion protein, readily produced in commercially significant quantities, that is an exceedingly sensitive and specific antigen for detection of HIV-1 antibodies.

It is yet another object of the present invention to provide a highly accurate diagnostic assay for detecting antibodies to HIV-1.

In accomplishing these and other objects, there has been provided, according to one aspect of the present invention, a fusion protein comprised of an amino acid sequence selected from the group consisting of NVTENFNMWKN, KAKRRVVQREKRAVG, ERYLKDQQLLGIWGCS-GKLIC and EESQNQQEKNEQELLELDKWA; and a non-HIV polypeptide sequence, such that the amino-acid sequence and the polypeptide sequence comprise the backbone of the fusion protein, wherein the fusion protein reacts with an HIV-positive serum. In a preferred embodiment, the amino-acid sequence is joined via a peptide bond to an N-terminus of the non-HIV polypeptide sequence.

In accordance with another aspect of the present invention, a self-replicating cell is provided that expresses a polypeptide comprising an amino-acid sequence selected from the group consisting of NVTENFNMWKN, KAKRRVVQREKRAVG, ERYLKDQQLLGIWGCS-GKLIC and EESQNQQEKNEQELLELDKWA.

Also provided, according to still another aspect of the present invention, is a diagnostic assay for detecting the presence of anti-HIV antibody in a sample, comprising the steps of (A) immobilizing on a solid matrix a fusion protein comprising an amino-acid sequence, ERYLKDQQLLGI-WGCSGKLIC and a non-HIV polypeptide sequence, such that the amino-acid sequence is accessible to an antibody contacting a surface of the matrix; (B) bringing a sample into contact with the surface of the matrix; and (C) monitoring the surface for binding of HIV-specific antibody. In one preferred embodiment, step (C) comprises detecing the presence of anti-HIV antibody in a sample that tests HIV-negative when tested using a conventional whole-virus western blot assay.

Pursuant to another aspect of the present invention, a diagnostic assay is provided for detecting the presence of anti-HIV antibody in a sample, comprising the steps of (A) providing a fusion protein comprising an amino-acid sequence ERYLKDQQLLGIWGCSGKLIC and an amino acid sequence of an enzyme; (B) combining a sample with the fusion protein in a liquid; and (C) monitoring the combination for a modulation of activity of the enzyme.

A vaccine comprising a fusion protein, as described above, and a sterile, pharmacologically acceptable carrier therefor is also provided, in accordance with yet another aspect of the present invention.

In accordance with another aspect of the present invention, there has been provided an immunotherapy method that comprises the step of administering to a subject an immunostimulatory amount of a vaccine as described above. In a preferred embodiment, the subject is already infected with HIV-1 when the vaccine is administered.

Pursuant to another aspect of the present invention, an immunotherapy method is provided comprising the step of administering to a subject an immunostimulatory amount of a hyperimmune globulin prepared according to a method comprised of immunizing a plasma donor with a vaccine as described above, such that a hyperimmune globulin is produced which contains antibodies directed against HIV-1. According to another aspect of the present invention, an immunotherapy method is provided that comprises administering to a subject an immunostimulatory amount of a hyperimmune globulin prepared in the aforementioned manner.

Also provided is an immunotoxin conjugate comprising a fusion protein, as described above, conjugated to an immunotoxin. In addition, an immunotherapy method is provided, according to another aspect of the present invention, wherein a subject already infected with HIV-1 receives antibodies directed against a fusion protein of the invention, wherein the antibodies are conjugated to an immunotoxin.

According to still another aspect of the present invention, a composition is provided that consists essentially of antibodies that bind the aforementioned fusion protein. (In this context, the qualifier "consists essentially of" means that the composition may have other constituents, such as a pharmaceutically acceptable carrier for the antibodies, but that the salient properties of the composition are determined by the immunological characteristics of the antibodies.) In a preferred embodiment, the composition is a monoclonal antibody composition, while in another preferred embodiment the antibodies are not obtained by a process comprising the step of providing a biological sample from a human subject infected with HIV-1.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the oligonucleotide sequences coding for HIV88 (FIG. 1A), HIV500 (FIG. 1B), HIV582 (FIG. 1C) and HIV647 (FIG. 1D).

FIG. 2 shows the oligonucleotide sequences coding for SIV88 (FIG. 2A), SIV500 (FIG. 2B), SIV582 (FIG. 2C) and SIV647 (FIG. 2D). In both FIGS. 1 and 2, the encoded amino acids for the respective polypeptides are also shown, as are the recognition sites for restriction endonucleases, denoted above each site, which can be used to obtain the oligonucleotide sequences from the HIV-1 genome.

DESCRIPTION OF THE PREFERRED EMBODIMENTS

It has been discovered that certain short, highly conserved polypeptide sequences of gp41 and gp120, having from eleven to twenty-one amino acids, possess attributes making them suitable for use in the diagnosis, treatment and prevention of HIV infection. According to the present invention, these polypeptide sequences are joined, preferably via DNA recombinant techniques, to a non-HIV protein or polypeptide sequence comprising a sequence of amino acids not naturally found in the HIV genome, to form a fusion protein.

Fusion proteins comprising these sequences have been shown to be good candidates for an HIV vaccine. While vaccines comprising these sequences have not been tested in humans, for obvious reasons, their utility in this regard is indicated by results obtained when equivalent sequences derived from SIVmac env are used to immunize Rhesus monkeys, discussed more fully below. The HIV sequences according to the invention are denominated HIV88, HIV500, HIV582 and HIV647, and have the following amino acid sequences:

HIV88:
Asn-Val-Thr-Glu-Asn-Phe-Asn-Met-Trp-Lys-Asn (NVTENFNMWKN)

HIV500:
Lys-Ala-Lys-Arg-Arg-Val-Val-Gln-Arg-Glu-Lys-Arg-Ala-Val-Gly (KAKRRVVQREKRAVG)

HIV582:
Glu-Arg-Tyr-Leu-Lys-Asp-Gln-Gln-Leu-Leu-Gly-Ile-Trp-Gly-Cys-Ser-Gly-Lys-Leu-Ile-Cys (ERYLKDQQLLGIWGCSGKLIC)

HIV647:
Glu-Glu-Ser-Gln-Asn-Gln-Gln-Glu-Lys-Asn-Glu-Gln-Glu-Leu-Leu-Glu-Leu-Asp-Lys-Trp-Ala (EESQNQQEKNEQELLELDKWA)

One of these polypeptide sequences, HIV582, combines aspects of two previously delineated immunodominant epitopes of gp41 (RILAVERYLKDQQLLGIWGCS and LGIWGCSGKLIC), and can be incorporated into fusion proteins that are consequently recognized by virtually all HIV-positive sera. Surprisingly, it can be used to detect the presence of HIV-1-specific antibodies in sera that are obtained from patients recently infected by the virus and that test negative via whole-virus HIV-1 western blot and other conventional assays.

The identity of the non-HIV polypeptide to which the HIV polypeptide sequence is fused to form a fusion protein is not critical, but it preferably is one that can be expressed by a genetically-engineered microbe and purified from the culture medium. Exemplary of this group of polypeptides is β-galactosidase, protein G, acetylchloramphenicol transferase, tryptophan synthetase, influenza A nonstructural protein (NS1), hepatitis core and surface antigens, and bacterial exotoxins such as E. coli LT, cholera toxin, and Pseudomonas toxin A. Particularly preferred are non-HIV polypeptides that possess an enzymatic property that can be exploited for purification and/or diagnostic purposes. Enzyme activity permits easier monitoring of purification. In addition, polypeptides according to the present invention in which the HIV582 is fused to an enzyme can form the basis for a simplified diagnostic assay using a homogenous system in which modulation of enzyme activity is monitored.

β-galactosidase is particularly preferred as the non-HIV polypeptide fused to the HIV polypeptide sequence for other reasons. In addition to the advantages arising the fact that it is an enzyme, it possesses other beneficial attributes. Since it is a tetramer it can hold four epitopes. Another significant advantage, and one that is entirely unexpected, is the fact that most people do not have any antibodies to β-galactosidase.

When an HIV polypeptide sequence is fused to β-galactosidase, the β-galactosidase acts as an immunocarrier, i.e., a substance, usually a polypeptide or protein, which is critical for the efficient interaction between T and B cells for the induction of an immune response against a small antigen that is attached to it.

A fusion protein within the present invention incorporates the HIV polypeptide sequence into the primary structure ("backbone") of the protein. It is preferred that the HIV polypeptide sequence be joined, via a peptide bond between the terminal carboxyl group of the HIV sequence and the terminal amino group of the non-HIV polypeptide. This arrangement enhances the possibility of a reaction between the fusion protein and antibodies that develop as a consequence of HIV-1 infection. Moreover, the arrangement is efficient in inducing an immune response that is specific for HIV-1.

The fusion proteins of the present invention can be produced by conventional genetic-engineering techniques. In this regard, a polynucleotide molecule encoding the desired protein preferably comprises a nucleotide sequence, corresponding to one of the amino-acid sequences according to the invention, that is optimized for the host of choice, such as *E. coli,* in terms of codon usage and initiation of translation. In the same vein, the vector selected for transforming the host organism with the polynucleotide molecule should allow for efficient maintenance and transcription of the sequence coding for the fusion protein.

Fusion proteins comprising HIV582 are particularly useful in various immunoassays which detect the presence of antibodies indicative of a particular disease state. For example, western blot and ELISA immobilize the polypeptides on a solid matrix and then contact the immobilized polypeptide with a sample.

The acronym ELISA refers to "enzyme-linked immunosorbent assay," that is, an assay using an antigen or antibody bound to a solid phase and an enzyme-antibody or enzyme-antigen conjugate to detect and/or quantify antibody or antigen present in a sample. In western blot assays, solubilized and separated antigens are bound to nitrocellulose paper. The antibody is detected by an enzyme or label-conjugated anti-immunoglobulin (Ig), such as horseradish peroxidase-Ig conjugate and detected by incubating the filter paper in the presence of a precipitable or detectable substrate. Western blot assays have the advantage of not requiring purity greater than 50% for the desired polypeptide. Descriptions of the ELISA and western blot techniques are found in Chapters 10 and 11 of Ausubel, et al. (eds.), CURRENT PROTOCOLS IN MOLECULAR BIOLOGY, John Wiley and Sons (1988), the contents of which are hereby incorporated by reference.

The present invention also relates to the use of a fusion protein to produce antisera or monoclonal antibodies (mouse or human) that bind to or neutralize virus. These antibodies can be employed to produce immunotoxin conjugates (e.g., with a ricin A chain) which should be useful in therapy of HIV-1 infections. Protocols for producing these antibodies are described in Ausubel, et al. (eds.) loc. cit., Chapter 11; in METHODS OF HYBRIDOMA FORMATION 257–71, Bartal & Hirshaut (eds.), Humana Press, Clifton, N.J. (1988); in Vitetta et al., *Immunol. Rev.* 62: 159–83 (1982); and in Raso, *Immunol. Rev.* 62: 93–117 (1982).

Inocula for polyclonal antibody production are typically prepared by dispersing the dried solid HIV sequence-immunocarrier in a physiologically tolerable diluent such as saline to form an aqueous composition. An immunostimulatory amount of inoculum is administered to a mammal and the inoculated mammal is then maintained for a time period sufficient for the HIV sequence to induce protecting anti-HIV-1 antibodies.

Antibodies can include antiserum preparations from a variety of commonly used animals, e.g., goats, primates, donkeys, swine, rabbits, horses, hens, guinea pigs, rats or mice, and even human antisera after appropriate selection and purification. The animal antisera are raised by inoculating the animals with an immunogenic form of the pathogen or its antigen, by conventional methods, bleeding the animals and recovering serum or an immunoglobulin-containing serum fraction.

The antibodies induced in this fashion can be harvested and isolated to the extent desired by well known techniques, such as by immunoaffinity chromatography; that is, by binding antigen to a chromatographic column packing like Sephadex®, passing the antiserum through the column, thereby retaining specific antibodies and separating out other immunoglobulins and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the serum of patients having developed an antibody titer against the pathogen in question, thus assuring the retention of antibodies that are capable of binding to exposed epitopes. They can then be used in preparations for passive immunization against HIV-1 or in diagnostic assays.

A monoclonal antibody composition contains, within detectable limits, only one species of antibody combining site capable of effectively binding HIV-1 TMP. In particular, a monoclonal antibody composition of the present invention typically displays a single binding affinity for HIV-1 TMP even though it may contain antibodies capable of binding proteins other than HIV-1 TMP.

Suitable antibodies in monoclonal form can be prepared using conventional hybridoma technology. To form a hybridoma from which a monoclonal antibody composition of the present invention is produced, a myeloma or other self-perpetuating cell line is fused with lymphocytes obtained from peripheral blood, lymph nodes or the spleen of a mammal hyperimmunized with a polypeptide of this invention. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines P3X63-Ag8.653 and Sp2/0-Ag14, available from the American Type Culture Collection, Rockville, Md., under the designations CRL 1580 and CRL 1581, respectively. The preferred fusion partner for human monoclonal antibody production is SHM-D33, a heteromyeloma available from ATCC, Rockville, Md. under the designation CRL 1668.

A monoclonal antibody composition of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hydridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal essential medium supplemented with 4.5 g/l glucose, 20 mm glutamine, and 20% fetal calf serum. An exemplary inbred mouse strain is the Balb/c.

Other methods of preparing monoclonal antibody compositions are also contemplated, such as interspecies fusions and genetic engineering manipulations of hypervariable regions, since it is primarily the antigen specificity of the antibodies that affects their utility in the present invention. Human lymphocytes obtained from HIV-infected individuals can be fused with a human myeloma cell line to produce hybridomas which can be screened for the production of antibodies that recognize a fusion protein of the present invention. More preferable in this regard, however, is a process that does not entail the use of a biological sample from a human subject infected with HIV-1. For example, a subject immunized with a vaccine as described herein can serve as a source for antibodies suitably used in an antibody composition within the present invention.

The monoclonal and polyclonal antibody compositions produced according to the present description can be used to induce an immune response for the prevention or treatment of HIV infection. They can also be used in diagnostic assays where formation of an HIV-1 TMP-containing immunoreaction product is desired.

In this regard, the antibody component can be polyspecific, that is, it can include a plurality of antibodies that bind to a plurality of epitopes represented by the various conserved polypeptide sequences described above. The polyspecific antibody component can be a polyclonal antiserum, preferably affinity purified, from an animal which has been challenged with a fusion protein of the present invention and, hence, stimulated to produce a plurality of specific antibodies against the fusion protein. Another alternative is to use an "engineered polyclonal" mixture, which is a mixture of monoclonal antibodies with a defined range of epitopic specificities.

In both types of polyclonal mixtures, it can be advantageous to link polyspecific antibodies together chemically to form a single polyspecific molecule capable of binding to any of several epitopes. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, LABELED ANTIBODIES IN BIOLOGY AND MEDICINE 321–23, McGraw-Hill Int'l Book Co. (1978); Nisonoff, et al., *Arch Biochem. Biophys.* 93: 470 (1961); and Hammerling, et al., *J. Exp. Med.* 128: 1461 (1968); and in U.S. Pat. No. 4,331,647.

Other methods are known in the art to make bivalent fragments that are entirely heterospecific, e.g., use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art.

An antibody component produced in accordance with the present invention can include whole antibodies, antibody fragments, or subfragments. Antibodies can be whole immunoglobulin (IgG) of any class, e.g., IgG, IgM, IgA, IgD, IgE, chimeric antibodies or hybrid antibodies with dual or multiple antigen or epitope specificities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like *E. coli*. A lambda vector system is available thus to express a population of Fab's with a potential diversity equal to or exceeding that of subject generating the predecessor antibody. See Huse, W. D., et al., *Science* 246: 1275–81 (1989), the contents of which are hereby incorporated by reference.

A polypeptide according to the present invention can be the active ingredient in a composition, further comprising a pharmaceutically acceptable carrier for the active ingredient, which can be used as a vaccine to induce a cellular immune response and/or production in vivo of antibodies which combat HIV-1 infection. In this regard, a pharmaceutically acceptable carrier is a material that can be used as a vehicle for administering a medicament because the material is inert or otherwise medically acceptable, as well as compatible with the polypeptide active agent, in the context of vaccine administration. In addition to a suitable excipient, a pharmaceutically acceptable carrier can contain conventional vaccine additives like diluents, adjuvants, antioxidants, preservatives and solubilizing agents.

Pursuant to the present invention, such a vaccine can be administered to a subject not already infected with the virus, thereby to induce an HIV-protective immune response (humoral or cellular) in that subject. Alternatively, a vaccine within the present invention can be administered to a subject in which HIV-1 infection has already occurred but is at a sufficiently early stage that anti-HIV antibodies produced in response to the vaccine effectively inhibit further spread of infection.

By another approach, a vaccine of the present invention can be administered to a subject who then acts as a source for globulin, produced in response to challenge from the specific vaccine ("hyperimmune globulin"), that contains antibodies directed against HIV-1. A subject thus treated would donate plasma from which hyperimmune globulin would then be obtained, via conventional plasma-fractionation methodology, and administered to another subject in order to impart resistance against or to treat HIV-1 infection. Similarly, monoclonal or polyclonal anti-HIV-1 antibodies produced using a fusion protein according to the present invention can be conjugated to an immunotoxin, as described above, and administered to a subject in whom HIV-1 infection has already occurred but has not become widely spread. To this end, antibody material produced pursuant to the present description would be administered in a pharmaceutically acceptable carrier, as defined herein.

The present invention is further described below by reference to the following, illustrative examples. In keeping with standard polypeptide nomenclature, the following abbreviations shown below for amino acid residues are used.

| TABLE OF CORRESPONDENCE | | | | | |
|---|---|---|---|---|---|
| Ala | A | Alanine | Leu | L | Leucine |
| Arg | R | Arginine | Lys | K | Lysine |
| Asn | N | Asparagine | Met | M | Methionine |
| Asp | D | Aspartic acid | Phe | F | Phenylalanine |
| Cys | C | Cysteine | Pro | P | Proline |
| Glu | E | Glutamic Acid | Ser | S | Serine |
| Gln | Q | Glutamine | Thr | T | Threonine |
| Gly | G | Glycine | Trp | W | Tryptophan |
| His | H | Histidine | Tyr | Y | Tyrosine |
| Ile | I | Isoleucine | Val | V | Valine |

In order to test the level of antibody production elicited by the administration of a polypeptide of the present invention, two different protocols were used. In the first, Rhesus monkeys were immunized with an HIV sequence fused to β-galactosidase, and the antibody titer was measured at various times after immunization.

In the second technique, sequences were identified from SIVmac (Simian Immunodeficiency Virus) env that are equivalent, according to the following criteria, to the sequences set forth in Table 1. SIV peptide sequences on SIVmac env that appeared in a location similar to that found in the primary sequence of HIV-1 env, which were also hydrophilic and at least about 50% homologous to the sequence to the HIV-1 env peptide, were selected.

Of the six epitopes shown in Table 1 below, only three SIVmac env sequences, SIV88, SIV582 and SIV647, satisfied all three criteria. A fourth SIV sequence, SIV500, which showed only about 25% homology to HIV500, was also selected, because this epitope was found to be an immunodominant C-terminal epitope on HIV-1 gp120. SIV500 corresponds to the putative C-terminal SIV gp120 sequence. Like HIV500, it was hydrophilic.

Because of the criteria used to correlate HIV and SIV sequences, observation of the antibody response of monkeys immunized with an SIV sequence could be used to assess the antibody response of humans immunized with the corresponding HIV sequence. The four SIV polypeptide sequences selected are shown below.

SIV88:
Asn-Val-Thr-Glu-Ser-Phe-Asp-Ala-Trp-Glu-Asn (NVTESFDAWEN)

SIV500:
Arg-Tyr-Thr-Thr-Gly-Gly-Thr-Ser-Arg-Asn-Lys-Arg (RYTTGGTSRNKR)

SIV582:
Glu-Lys-Tyr-Leu-Glu-Asp-Gln-Ala-Gln-Leu-Asn-Ala-Trp-Gly-Cys-Ala-Phe-Arg-Gln-Val-Cys (EKYLEDQAQLNAWGCAFRQVC)

SIV647:
Glu-Glu-Ala-Gln-Ile-Gln-Gln-Glu-Lys-Asn-Met-Tyr-Glu-Leu-Gln-Lys-Leu-Asn-Ser-Trp-Asp (EEAQIQQEKNMYELQKLNSWD)

EXAMPLE 1

Production and Purification of Recombinant Fusion Protein

From published amino-acid sequences, hydrophobicity plots of the HIV env encoded proteins were generated, and five domains were selected, each manifesting conservation of sequences and a high degree of hydrophilicity, and a high content of amino acids implicated in the determination of the secondary structure on a protein, such as cysteine, aromatic amino acids, proline and glycine. Sequences rich in hydrophobic residues were avoided, since highly hydrophilic regions are more likely to be antigenic than are hydrophobic regions. Three peptides, designated HIV88, HIV475 and HIV500 in Table 1 below, were selected from the $NH_2$-terminus and COOH-terminus of gp120, and two peptides from the $NH_2$-terminus portion of gp41 (HIV647 and HIV705 in Table 1). Also prepared was a sixth domain (HIV582 in Table 1) from gp41, combining aspects of two highly immunodominant sequences. See Wang, J. J. G., et al., loc. cit.; Gnann, J. W., et al., loc. cit.

Oligonucleotides coding for the HIV amino-acid sequences depicted in Table 1 were synthesized on a 381A DNA synthesizer (Applied Biosystems, Foster City, Calif.). The sequences of these oligonucleotides are shown in FIG. 1. The oligonucleotides were purified and inserted into plasmid $pTZ_2$ or a derivative thereof, pTOZ or pTIZ, pursuant to methodology of Shaffermann, A., et al., *J. Biol. Chem.* 262: 6227–37 (1987), the contents of which are hereby incorporated by reference. These plasmids were designed to accommodate various synthetic oligonucleotides in frame with the $NH_2$-terminus of β-galactosidase coding sequences, and to be expressed as fusion polypeptide under control of the *E. coli* trp promoter. See Ausubel, et al. (eds.), loc. cit., chapter 13, the contents of which are hereby incorporated by reference.

The synthetic oligonucleotides coding for HIV88 and HIV500 were cloned between the HindIII and PstI sites of pTOZ; HIV582, HIV647 and HIV705 between the NcoI and HindIII sites of pTOZ and HIV475 between the NdeI and HIndIII sites of $pTZ_2$. Correct constructs were verified by restriction enzyme analysis and DNA sequencing.

Strains of *E. coli* MC1060, see Casadaban, M. J., et al., "β-galactosidase gene fusions for analyzing gene expression in *E. coli* and yeast," in 100 METHODS OF ENZYMOLOGY 293–308 (Academic Press, New York), were transformed with the various HIV-pTOZ, HIV-PTIZ or HIV-$pTZ_2$ plasmids. The recombinant *E. coli* bacteria were maintained by serial passage on Lauria broth agar plates containing 50 μg/ml of ampicillin.

The *E. coli* were induced to express β-galactosidase under conditions described by Grosfeld, H., et al., loc. cit., and Shaffermann, A., et al., loc. cit. For scale up, an isolate was serially diluted in Lauria broth and ampicillin and allowed to grow overnight at 37 C with agitation. An inoculum from the overnight culture was transferred to a nutritionally deficient, defined medium (M9 media with limited L-tryptophane) and shaken vigorously at 37 C until an optical density of 3.0 ($A_{550}$) was achieved.

The cultured bacteria were centrifuged and the supernatant was discarded. The resulting pellet was treated with lysozyme for 30 minutes, and lysed by serial freezing and thawing. The lysate was centrifuged at high speed and the supernatant was recovered.

Recombinant protein of the present invention was precipitated from the lysate using ammonium sulfate. The level of production for each HIV-gal was in range of 2% to 10% of total bacterial proteins. Optimal recovery was found in the 40% cut. The precipitate was resuspended in a Tris buffer containing 2-mercaptoethanol, and dialyzed to remove excess salts. The resulting solution contained approximately 50% pure recombinant protein, mixed with other *E. coli* proteins of nonrecombinant origin, as characterized by Coomasie blue stained SDS-PAGE gels.

In a conventional manner, recombinant protein of the present invention can be further purified by affinity chromatography, as necessary, by use of a gel matrix upon which is immobilized, as a ligand, monoclonal antibody against beta-galactosidase. Alternatively, the fusion protein can be purified by high-performance liquid chromatographic ion exchange (DEAE5PW Waters Column), yielding over 98% pure protein. Either method would yield fusion protein with greater than 95% purity.

SIV recombinant fusion proteins were made in a similar manner, with oligonucleotides coding for the equivalent SIV amino-acid sequences being used. These oligonucleotides are shown in FIG. 2. Sequences of the SIV envelope are according to those published for SIVmac. See Franchini, G., et al., *Nature* 328: 539–42 (1987).

EXAMPLE 2

Evaluation of Reactive Specificity for Selected Domains of HIV Envelope Protein

As a first step in evaluation of the selected HIV env conserved domains, the reactivity of the six different HIV-gal fusion polypeptides was analyzed with specific panels of HIV-seropositive sera collected from various stages of HIV infection.

Serum samples were collected from patients having two separate serum specimens positive for anti-HIV antibodies by ELISA and western blot. See Redfield, R. R., et al., *New Engl. J. Med.* 314: 131–32 (1986). Virus-positive samples were defined as those in which a simultaneous culture of the patient's peripheral blood monocytes (PBMCs) yielded a positive culture by either RT activity or antigen capture, according to Gallo, D., et al., *J. Clin. Microb.* 25: 1291–94 (1987).

To assay the sera, an equivalent of 15 ng of HIV peptides (0.7–1.5 µg of 98% pure HIV-β-galactosidase) were dotted in duplicates on nitrocellulose filter disks. Filters were blocked with 1% casein/BSA for 2 hours at room temperature and then incubated for 18 hours at room temperature with four fold serial dilutions of sera, starting from a dilution of 1:100. Filters were washed and incubated with goat anti-(IgG, IgM) human antibodies conjugated to phosphatase (Kirkegaard Perry) at a final concentration of 3 ng/ml and developed (with Fast red TR salt and naphthol AS-MX phosphate Sigma) for 30 minutes. Each filter was dotted with all the HIV-βgal proteins as well as with a control of β-galactosidase. The end point of titration was determined by three individuals. Out of a total of 1360 readings of HIV-gal titrations, complete accordance was achieved in 1350 cases.

As shown in Table 1, each of the HIV-derived peptides were recognized by antibodies elicited in some or all the HIV-infected individuals. None of the twenty control sera reacted with the HIV-βgal polypeptides.

TABLE 1

Amino Acid Sequence of Various HIV-β-Galactosidase Fusion Proteins and Their Reactivities with HIV Seropositive Sera.

| HIV-gal | HIV-Amino Acid Sequence | Number Positive/Total (percent positive) |
|---|---|---|
| HIV88 | NVTENFNMWKN | 32/75 (43) |
| HIV475 | MRDNWRSELYKYKV | 8/30 (27) |
| HIV500 | KAKRRVVQREKRAVG | 36/75 (48) |
| HIV582 | ERYLKDQQLLGIWGCSGKLIC | 75/75 (100) |
| HIV647 | EESQNQQEKNEQELLELDKWA | 25/30 (83) |
| HIV705 | VNRVRQGYSPLSFQT | 5/30 (17) |

In general, a decrease in titers against the HIV domains tested heretofore has been observed with progression of disease. It is significant as well as unexpected, therefore, that all of the HIV-positive sera not only reacted with HIV582, but also responded in titers ($10^{-5}$) that were almost two orders of magnitude higher than any of the other conserved envelope regions (see Table 2). By contrast, HIV500, which overlaps most of the sequences of SP22 previously identified as a major immunodominant epitope on gp120 by Parker, T. J., et al., loc. cit., was recognized in only 48% of HIV positive sera and only elicited an antibody titer in the range of 1:1500 in the HIV-infected individual.

The increased magnitude of response is a result of the high level of expression of HIV582 at all stages of infection as compared to other epitopes. This difference in level of expression vis-a-vis other epitopes is especially high during early stages of infection, allowing HIV582 to successfully detect infection at a much earlier stage that other epitopes. The HIV582 sequence is thus shown to provide a sensitive tool for diagnostic purposes, capable of detecting very early stages of infection.

TABLE 2

Differential Reactivities of HIV-βgal Polypeptides with Sera from WR Stages 1 & 2 Versus WR Stages 5 & 6.

| HIV-βgal | Positive/Total (%) | | Geometric Mean Titer of Positive Specimens | |
|---|---|---|---|---|
| | WR 1 & 2 | WR 5 & 6 | WR 1 & 2 | WR 5 & 6 |
| HIV88 | 29/47* (62) | 3/28* (11) | 1:780 | 1:1,260 |
| HIV475 | 6/17 (35) | 2/13 (15) | 1:710 | 1:200 |
| HIV500 | 25/47 (53) | 11/28 (39) | 1:1,450 | 1:1,000 |
| HIV582 | 47/47 (100) | 28/28 (100) | 1:140,000 | 1:78,000 |
| HIV647 | 14/17 (82) | 11/13 (85) | 1:3,600 | 1:1,550 |
| HIV705 | 4/17 (23) | 1/13 (8) | 1:1,000 | 1:600 |

*Difference in proportion positive is statistically significant (p < 0.00001 by Fisher Exact test).

Of the two other conserved epitopes in gp41 that have been studied, the one within HIV647 also seems to be immunodominant. HIV647-βgal was recognized by 83% of HIV positive tested sera in any stage of the disease and in relatively high titers, as shown in Table 2. On the other hand, no reaction with HIV-positive sera was observed when a very similar peptide, CQNQQEKNEQELLE, was used. Gnann, J. W., et al., loc. cit. This may reflect the presence of the extra amino acids in HIV647, or it may result from the higher sensitivity of the immunodot method used. Alternatively, it may be that the coupling of this peptide to keyhole limpet hemocyanin results in conformational changes not occurring in HIV647-βgal.

Further study was made of an additional 45 sera from patients whose PBMCs were cultured for virus isolation, following Gallo, D., et al., *J. Clin. Microbiol.* 25: 1291–94 (1987). Within this group studied, twenty patients were virus isolation-negative (all in Walter Reed stages 1 or 2) and twenty-five patients were virus isolation-positive (ten in WR stages 1 or 2, and fifteen in WR stages 5 or 6). Since success of virus isolation is only 10–15% from PBMC specimens from patients in early stage disease, but close to 100% from patients in late stage disease, the sera selected for testing were intentionally biased in favor of virus culture-positive, early-stage patients.

As shown in Table 3, thirteen of the twenty HIV culture-negative patients (65%) had detectable HIV88-βgal reactivity, while only five of twenty-five sera from HIV isolation-positive patients had detectable HIV88-βgal antibodies (p<0.003). Among sera from early-stage patients (WR 1 or 2) only, thirteen of twenty specimens from virus culture-negative patients had HIV88-βgal reactivity, compared to only three of ten virus culture-positive patients (p=0.077). Antibodies to HIV500-βgal and HIV582-βgal were detected equally often in sera from virus isolation-positive and -negative patients. But unlike HIV500, HIV582 was positive in every tested case, regardless of the stage of the disease or the ability to detect virus in PBMC culture.

TABLE 3

Distribution of Reactivities of HIV-βgal Polypeptides with Selected Sera from Patients with Positive or Negative Virus Isolation from PBMCs.

| | Patient Sera | | |
|---|---|---|---|
| HIV-βgal | Stage 1–2 Virus Neg | Stage 1–2 Virus Pos | Stage 5–6 Virus Pos |
| HIV-88 | 13/20 | 3/10 | 2/15 |
| HIV-500 | 9/20 | 6/10 | 4/15 |
| HIV-582 | 20/20 | 10/10 | 15/15 |

EXAMPLE 3

Antigenicity of the Recombinant Protein Versus Known Synthetic Peptide Conjugated to Bovine Serum Albumin By means of a dot immunoassay, the antigenicity of the fusion protein was found to be far superior to a commercially synthesized peptide (Peninsula, Belmont, Calif.) which consisted of the same twenty-one amino acids of HIV582 conjugated to bovine serum albumin (BSA). This peptide conjugate was prepared such that BSA and the twenty-one amino acid sequence of HIV582 were present in equivalent weights, i.e., one mg of conjugate contained 500 ng of HIV582 and 500 ng of BSA. Ammonium sulfate-precipitated recombinant HIV antigen was used at 50% purity, and the weight of the HIV582 was calculated to be 10 ng/mg total protein in the antigen solution. The recombinant and peptide conjugate antigens were prepared as 1 mg/ml total protein solutions (determined by the Lowry method) and 5 µl samples of serially diluted antigen were applied to nitrocellulose paper, air dried, and blocked. It was confirmed that equivalent amounts of total protein were bound to the nitrocellulose by reaction with ninhydrin. The paper was incubated for four hours with serum containing HIV antibodies diluted 1:100, and antigen-bound antibody was detected with a peroxidase-conjugated secondary antibody system. The results are presented in Table 4, where the intensity of the visible dot was graded on a scale in which ± was a barely detectable reaction, and ++++ was an intensely dark dot on the nitrocellulose paper. These results indicate that the recombinant HIV582 antigen is at least 50 times more sensitive than the synthetic peptide conjugate that was used in the diagnostic assay.

TABLE 4

Comparison of Recombinant HIV582-βgal and Synthetic HIV582-BSA Conjugate.

| Recombinant HIV582-βgal | | Synthetic HIV582-BSA | |
|---|---|---|---|
| Antigen (ng) | Reactivity | Antigen (ng) | Reactivity |
| 50 | ++++ | 2500 | ++++ |
| 25 | ++++ | 1250 | ++++ |
| 12.5 | ++++ | 625 | +++ |
| 6.25 | ++++ | 312.5 | +++ |
| 3.13 | +++ | 156.25 | ++ |
| 1.57 | +++ | 78.12 | ++ |
| 0.78 | ++ | 39.10 | + |
| 0.39 | + | 19.55 | +/− |

EXAMPLE 4

Comparative Study of Fusion Protein-Based Western Blot and Conventional Whole-Virus HIV-1 Western Blot Western blot strips containing the fusion protein were prepared by SDS-PAGE followed by transfer to nitrocellulose paper. Strips containing approximately 2 µg of fusion protein were cut from the nitrocellulose strips and used to characterize a pool of 400 sera from HIV-infected patients as determined from clinical symptoms, whole-virus western blot or virus isolation, and 500 HIV-negative sera at 1:100 dilution. All 400 HIV-positive samples reacted with the fusion protein, while none of the 500 negative samples reacted with the antigen. The specificity and sensitivity of the test with this sample population were thus 100%.

A subpopulation of 104 sera from the pool of 400 was characterized using a the conventional whole-virus HIV-1 western blot (DuPont). According to the manufacturer, the presence of antibodies to three specific antigens, gag, env and RT, are required for a positive diagnosis. Many physicians, however, positively diagnose the disease based on the presence of antibodies to only two antigens, env and either gag or RT. The results with the whole-virus western blot are shown in Table 5.

TABLE 5

Sera Reactivity with Whole-virus Western Blot.

| Antigen | Number of Sera |
|---|---|
| gag, env and RT | 84 |
| env and gag or env and RT | 11 |
| env only | 4 |
| gag only | 4 |
| no reaction | 1 |

Thus, even under the more relaxed "two out of three" criteria, the conventional whole-virus western blot gives a false negative in over 8% of the samples. Most importantly, the whole virus failed to identify one of the sera as positive under any criteria. This individual was later identified as HIV positive when results of his virus isolation were complete.

The diagnostic assay based on HIV582 correctly identified all 104 infected individuals. Thus, the HIV582 assay identifies infected individuals that do not give a positive reaction with any of the three antigens used in whole virus western blot assay, allowing HIV positive individuals to be identified at an earlier stage of infection.

EXAMPLE 5

Antibody Titers to Various SIVmac env Peptides in Plasma from Different Macaque Species Infected with SIVMne Three juvenile Rhesus macaques (*M. mulatta*), three juvenile pigtailed macaques (*M. nemestrina*), and two cynomolgus macaques (*M. fascicularis*) were inoculated intravenously with $10^3$ TCID of SIV/Mne. See Shaffermann, A., et al., *J. Aids Res.* 5: 327–26 (1989), the contents of which are incorporated herein by reference. All macaques became viremic within three weeks after inoculation, and all mounted an antibody response to SIV/Mne except *M. nemestrina* T85056, which died at fifteen weeks with an ulcerative necrotizing colitis and a marked decrease in CD4+ PBL. The other macaques died 43–121 weeks after inoculation after exhibiting progressive weight loss, anemia, and diarrhea. Histopathologic findings at necropsy included various manifestations of immune deficiency.

The development of antibodies of SIV/Mne was determined by estern immunoblotting at various times after inoculation, and is tabulated in Table 5. Seven macaques developed readily detectable antibodies by 5–6 weeks after inoculation, with antibodies to gag p28 and to the transmembrane protein p34E generally appearing before antibodies to other gene products was detected. At various times after inoculation, antibodies to gp120 (the envelope protein) and to gag proteins p16, p8 and p6 were also evident. In addition, some of the macaques developed antibodies to p14, which has been identified as the product of the X-orf gene of SIV.

Prior to inoculation of monkeys with SIV/Mne, none of the primate sera (dilution 1:100) reacted with the SIVmac env-gal polypeptides, yet all SIVmac env-βgal polypeptides reacted with antibodies elicited in all the post-SIV/Mne infected monkeys. Pig-tailed macaque T85056, although viremic, remained antibody-negative after inoculation. Plasma from this animal did not react with the SIVmac env-βgal polypeptides. The order of both antibody prevalence to the various SIV env epitopes and the immunogenicity of these epitopes in SIV-infected macaques is SIV-582>SIV-647>SIV-500>SIV-88. The order of antibody prevalence and of immunogenicity of these envelope epitopes is identical to that found for the equivalent HIV envelope epitopes in humans infected with HIV-1.

The results show that the humoral response in macaques infected with SIVMne to the specific SIVmac envelope epitopes parallels that observed for the equivalent HIV env epitopes in humans infected with HIV. This shows that the SIV macaque system is a suitable model for assessing HIV vaccines and other immunotherapies for AIDS.

TABLE 5

Antibody response to SIVmac env peptides from macaques infected with SIVMne.

| Animal | Weeks after infection | SIV88 | SIV500 | SIV582 | SIV647 |
|---|---|---|---|---|---|
| *M. mulatta* | | | | | |
| A85033 | 9 | <1:100 | <1:100 | 1:6400 | <1:100 |
|  | 36 | <1:100 | 1:200 | 1:100K | <1:100 |
|  | 66 | <1:100 | <1:100 | 1:100K | 1:400 |
| A85034 | 14 | <1:100 | <1:100 | 1:25K | <1:200 |
|  | 36 | <1:100 | <1:100 | 1:50K | 1:1600 |
|  | 87 | <1:100 | <1:100 | 1:200K | 1:6400 |
| A85037 | 14 | <1:100 | 1:400 | 1:1600 | <1:100 |
|  | 36 | <1:100 | 1:1600 | 1:25K | <1:100 |
|  | 95 | <1:100 | 1:1600 | 1:6400 | 1:100 |
| *M. nemestrina* | | | | | |
| F85062 | 18 | <1:100 | 1:400 | 1:100K | 1:600 |
|  | 36 | 1:400 | 1:400 | 1:400K | 1:1600 |
|  | 80 | <1:100 | 1:400 | 1:100K | 1:1600 |
| M85026 | 18 | 1:400 | <1:100 | 1:25K | 1:6400 |
|  | 66 | 1:400 | <1:100 | 1:100K | 1:100K |
|  | 120 | 1:200 | <1:100 | 1:100K | 1:400K |
| *M. fascicularis* | | | | | |
| 85175 | 12 | 1:100 | 1:100 | 1:6400 | 1:100 |
|  | 37 | 1:100 | 1:100 | 1:12,500 | <1:100 |
|  | 51 | 1:400 | <1:100 | 1:50K | <1:100 |
| 85176 | 12 | 1:200 | 1:1600 | 1:25K | 1:200 |
|  | 24 | 1:400 | 1:3200 | 1:100K | 1:400 |
|  | 43 | 1:200 | 1:6400 | 1:100K | 1:400 |

*Plasma from all macaques were seronegative for all SIV env-gal polypeptides at a dilution of 1:100 prior to inoculation with SIVMne.

EXAMPLE 6

Immunization of *M. mulatta* with HIV647-βgal

Three groups of monkeys (3 animals/group) were immunized with different doses of HIV647-βgal: 4, 40 and 400 μg (95% HPLC pure). On day zero, each animal received complete Freund's, on day 14 each animal received incomplete Freund's, and on day 35 each animal received soluble antigen only. Adjuvant was mixed (0.5 ml with 0.5 ml HIV-βgal prior to inoculation. Monkeys were inoculated intra-muscularly at four sites with 0.25 ml per site.

The antibody response was measured by an immunodot test in which 1.0 μg of 98% pure antigen (HIV647-βgal, HIV88-βgal and βgal) was dotted in duplicate on nitrocellulose filters. The filters were blocked with 1% casein/BSA for two hours. Diluted sera were preincubated with βgal, at concentrations of 200–80 μg/ml, for one hour at 37° C. and then incubated for eighteen hours at room temperature with the filters. Filters were washed, then incubated with goat anti-human phosphatase antibodies (3 ng/ml) for three hours and developed for nine minutes.

An ELISA was also performed with a synthetic twenty amino acid peptide of the HIV647 epitope. ELISA was performed on PVC plates preincubated with 4 μg/ml of a cys-647 HIV peptide, a synthetic peptide of HIV647 to which a cysteine residue was added at the N-terminus. Linearity of OD readings with sera dilution was not observed. Differential (Day x–Day zero) OD values for each dilution were used to determine the endpoint. A significant differential OD value was considered to be that which was threefold higher than that obtained from the differential value of Day 14–Day Zero and above a cutoff value of 0.040. No attempt was made to optimize the sensitivity of the ELISA.

On day zero, no sera had detectable antibody to HIV647 at a serum dilution of 1:100 with immunodot or 1:8 with ELISA. On day 14, all sera had titers lower than 1:1000. None of the sera reacted with a control of HIV88-βgal. The antibody titers on days 28 and 51 as measured by both immunodot and ELISA are shown in Table 7.

TABLE 6

Antibody response to HIV647-βgal measured by immunodots and ELISA.

| | | Immunodot Titer | | ELISA titer | |
|---|---|---|---|---|---|
| Dose | Animal | Day 28 | Day 51 | Day 28 | Day 51 |
| 4 | T313 | 1:2000 | 1:64K | <1:8 | 1:256 |
| 4 | O27A | 1:16K | 1:64K | 1:512 | 1:1024 |
| 4 | T324 | <1:1000 | 1:32K | <1:8 | 1:1024 |
| 40 | O5 | 1:4000 | 1:32K | <1:8 | <1:8 |
| 40 | X662 | 1:16K | 1:64K | 1:64 | 1:128 |
| 40 | T308 | n.m. | n.m. | 1:128 | 1:128 |
| 400 | T34 | 1:16K | 1:32K | 1:32 | 1:128 |
| 400 | P792 | 1:8000 | 1:16K | 1:16 | 1:128 |
| 400 | A32 | 1:2000 | 1:64K | <1:8 | 1:128 | n.m. - not measurable due to βgal background

The fact that the sera reacted with HIV647-βgal, but not with HIV88-βgal, indicates that the response is specific to HIV647. The ELISA results confirm that, while HIV647-βgal is composed of both HIV647 and βgal, antibodies are produced against the HIV647 sequence.

The antibody response to the βgal immunocarrier was also measured by immunodot titration. All sera on day zero had anti-βgal titers lower than 1:50. The results on days 14, 28 and 51 are shown in Table 7.

TABLE 7

Antibody response to the βgal immunocarrier.

| | | Immunodot Titer | | |
|---|---|---|---|---|
| Dose | Animal | Day 14 | Day 28 | Day 51 |
| 4 | T313 | <1:500 | 1:50K | 1:250K |
| 4 | O27A | <1:500 | 1:50K | 500K |
| 4 | T324 | <1:500 | 1:500 | 1:25K |
| 40 | O5 | 1:5000 | 1:50K | 1:50K |
| 40 | X662 | 1:5000 | 1:250K | 1:250K |
| 40 | T308 | 1:500 | 1:50K | 1:50K |
| 400 | T34 | 1:500 | 1:250K | 1:250K |
| 400 | P792 | 1:25K | 1:50K | 1:100K |
| 400 | A32 | 1:5000 | 1:25K | 1:250K |

The HIV647-βgal elicited antibodies that recognized specifically not only HIV647-βgal, but also the twenty-two amino acid HIV647 peptide. The results show that the HIV647 epitope is very immunogenic and βgal is a potent immunocarrier in monkeys. Specific immune response to the HIV647 epitope was obtained when as little as 4 μg of the fusion protein, equivalent to only 80 ng of the HIV sequence, is used. In immunodots the titer of anti-HIV647 antibodies was 1:64000, which was only fivefold lower than the titer obtained against the large (400,000-dalton) βgal tetramer.

No suppression of the immune response was observed when 4 to 400 μg was used. Titers to βgal reached a level of 1:250000, independent of the dose. The boost with soluble antigen was most significant at the lowest dose. Also, a somewhat higher anti-HIV647 antibody titer was obtained at the lowest dose of βgal.

EXAMPLE 7

Immunization of HIV647-βgal Preimmunized *M. mulatta* with HIV582-βgal

Three Rhesus monkeys from Example 6, T313, 027A and T324, were immunized with 4 μg of HIV582-βgal, according to the protocol of Example 6. The antibody titers to both HIV647-βgal and HIV582-βgal as measured by immunodot are shown in Table 8.

TABLE 8

Antibody response HIV647-βgal and HIV582-βgal.

| | HIV647-βgal Titer | | | HIV582-βgal titer | |
|---|---|---|---|---|---|
| Animal | Day 51 | Day 147* | Day 190 | Day 147* | Day 190 |
| T313 | 1:64K | 1:16K | 1:16K | <1:100 | 1:8000 |
| O27A | 1:64K | 1:8000 | >1:16K | <1:100 | >1:16K |
| T324 | 1:32K | 1:1000 | 1:2000 | <1:100 | 1:1000 |

*Day 147 is day 0 for immunization with HIV582-βgal

The results show that HIV582 is also an immunogenic epitope in Rhesus monkeys. Preimmunization with HIV647-βgal did not prevent effective immunization with HIV582-βgal. The moderate increase in HIV647 titer indicates that the use of the same immunocarrier in consecutive immunizations of two different HIV epitopes helps memory cells generated from the first immunization.

EXAMPLE 8

Immunization of *M. mulatta* with SIV-βgal Fusion Proteins

Three groups of monkeys (3 animals/group), free of antibodies to both HIV and SIV, were used. Each group was immunized according to the protocol of Example 6. In each case 4 μg of antigen was used in the immunization. One group (animal 3X7, 4GP and 4GI) was immunized with a mixture of the four different SIV-βgal polypeptides (SIV88, SIV500, SIV582 and SIV647). A second group was immunized with SIV647-βgal (4GN, 4GJ and 4GG) and a third group was immunized with βgal. As in Example 6, antibody titers were determined with both immunodot and ELISA. ELISA was performed, as described in Example 6, except that plates were coated with synthetic SIV peptides conjugated to BSA.

On day zero and day 14, no sera had detectable antibodies to any SIV epitope at a serum dilution of 1:100. On day 36, all titers were one-quarter to one-half the values on day 43, which are reported in Table 9. The antibody response to βgal is reported in Table 10.

TABLE 9

Antibody response to SIV epitopes in *M. mulatta* on day 43.

| Animal | Assay | SIV88 | SIV500 | SIV582 | SIV647 |
|---|---|---|---|---|---|
| 3X7 | Immunodot | 1:256K | 1:64K | 1:128K | 1:256K |
| | ELISA | 1:16 | | 1:512 | 1:1024 |
| 4GP | Immunodot | 1:256K | 1:64K | 1:64K | <1:256K |
| | ELISA | 1:256 | | 1:1024 | 1:512 |
| 4GI | Immunodot | 1:64K | 1:16K | 1:32K | 1:256K |
| | ELISA | 1:256 | | >1:1024 | 1:256 |
| 4GN | Immunodot | — | — | — | 1:128K |
| | ELISA | — | — | — | 1:1024 |

TABLE 9-continued

Antibody response to SIV epitopes in *M. mulatta* on day 43.

| Animal | Assay | SIV88 | SIV500 | SIV582 | SIV647 |
|---|---|---|---|---|---|
| 4GJ | Immunodot | — | — | — | 1:256K |
|  | ELISA | — | — | — | >1:1024 |
| 4GG | Immunodot | — | — | — | 1:256K |
|  | ELISA | — | — | — | 1:128 |

TABLE 10

Antibody response to the βgal immunocarrier.

| | Immunodot Titer | | | |
|---|---|---|---|---|
| Animal | Day 0 | Day 14 | Day 36 | Day 43 |
| 3X7 | <1:100 | 1:1000 | 1:400K | ≧1:400K |
| 4GP | <1:100 | 1:100 | 1:200K | ≧1:400K |
| 4GI | <1:100 | 1:25K | 1:400K | ≧1:400K |

The results demonstrate that all four SIV epitopes are immunogenic in Rhesus monkeys when presented as βgal fusion proteins. The immunodot and ELISA results show that antibodies were directed exclusively against the SIV moiety of the SIV-βgal. The ability of the anti-SIV-βgal monkey antibodies to react with SIVmne antigens was tested in western blots of whole disrupted virus and with $^{35}$S-methionine labelled SIVmne cell lysates in a RIP assay. It was found that the anti-SIV-βgal antibodies reacted with both the transmembrane (p32) and the envelope (gp110) of SIV. These results clearly demonstrate that presentation of SIV epitopes via βgal can elicit an immune response which mimics that of native virus antigens. However, none of the immune sera had any neutralizing activity against SIV virus in vitro.

The antibody titers for all SIV antigens ranged from 1:16000 to 1:256000. Considering that the SIV epitope constitutes only 1–2% of the molecular weight of the βgal immunocarrier, the titer level is exceptionally high. Antibody titers to the immunocarrier are approximately 1:400000.

The natural antibody response in monkeys infected with SIVmne are:

| SIV88 | <1:100–1:400 |
| SIV500 | 1:100–1:1600 |
| SIV582 | 1:25000–1:400000 |
| SIV647 | 1:400–1:6400 |

Thus, with the exception of SIV582, the immunization with all SIV-βgal tested elicited an antibody response 10–100 fold higher than that elicited against these epitopes by the virus itself.

Immunization with a combination of all four SIV-βgal fusion proteins did not produce antigenic competition. The level of specific antibodies to SIV647 was comparable when immunization was with SIV647-βgal alone or in combination with other fusion proteins.

EXAMPLE 9

Challenge of SIV-βgal Immunized *M. mulatta* with SIVmne

The three monkeys immunized with the combination of all four SIV-βgal fusion proteins (3X7, 4GI and 4GP) were boosted at day 290. The boost was performed with soluble antigen. Each monkey received 40 µg of each of the SIV-βgal peptides by intramuscular injection.

Twenty-one days after the boost, the monkeys were challenged with viable SIV. All three immunized monkeys developed serologic evidence of transient SIV infection, whereas all three control monkeys developed positive western blots to numerous viral antigens, had reverse transcriptase activity detectable in their sera on repeated occasions, and were positive for viral nucleic acid sequences, indicating the presence of ongoing SIV infection. The results are summarized in Table 11.

TABLE 11

Results of reverse transcriptase and western blot assays on sera of monkeys challenged with SIVmne.

| | Immunized monkeys | | | | | | Control Monkeys | | | | | |
|---|---|---|---|---|---|---|---|---|---|---|---|---|
| | 3X7 | | 4GI | | 4GP | | 4GC | | 4HS | | 3XP | |
| Day | RT | WB | RT | WB | RT | WB | RT | WB | RT | WB | RT | WB |
| −6 | − | | − | | − | | − | | − | | − | |
| 0 | − | | − | | − | | − | | − | | − | |
| 7 | − | | − | | − | | − | | − | | − | |
| 14 | − | | ND | | ND | | ND | | ND | | ND | |
| 21 | − | − | − | +(2) | − | − | − | − | ND | − | − | − |
| 27 | − | | + | | − | | + | | + | | + | |
| 41 | − | ±(1) | + | ++(2) | + | ++(3) | − | − | − | − | + | ++(3) |
| 55 | − | | − | | − | | + | | − | | + | |
| 64 | − | − | − | ++(4) | − | ±(3) | + | +++(4) | − | ++(4) | nd | ++(3) |
| 94 | − | | − | | − | | + | | − | | − | |

Day zero = SIVmne challenge day
RT - Cocultivation-Reverse Transcriptase assay
WB - Western blot performed on SIVmne partially purified lysate
(1) env p32
(2) env p32 and p28
(3) env p32 and gp110 as well as p28
(4) env p32 and gp110 as well as p28 and p16

One of the three immunized monkeys (3X7) never became virus positive and two were transiently positive. Unlike the controls, none of the three experimentally vaccinated animals showed evidence of infection (by RT) 55 days post challenge. Two of the three developed a booster response against only the antigens with which they were immunized, demonstrating that post-vaccination exposure to the virus was capable of inducing an anamnestic booster response to the vaccine.

The antibody titer for the monkeys was determined by ELISA. All samples were run in duplicate at a 1:400 dilution and read on a $V_{max}$ ELISA reader at 850 nm. The results, expressed as mOD/min by a kinetic read, are summarized in Table 12.

TABLE 12

Antibody titer of monkeys challenged with SIVmne.

| Animal | Days post challenge with SIVmne | | | | | | | | |
|---|---|---|---|---|---|---|---|---|---|
| | 1 | 14 | 21 | 28 | 41 | 55 | 84 | 118 | 148 | 174 |
| 4GI | 1.7 | 1.1 | nd | 10 | 9.2 | 8.0 | 6.4 | 7.1 | 5.8 | 5.8 |
| 4GP | 0.1 | 0.1 | nd | 0.9 | 6.0 | 0.8 | 1.1 | 1.7 | 1.8 | 1.6 |
| 3X7 | 0.2 | 0.2 | nd | 6.5 | 5.2 | 2.9 | 1.0 | 1.0 | 1.0 | 0.7 |
| 4GC | 0.1 | 0.1 | 0.6 | 3.1 | 1.4 | 8.6 | 15 | 12 | 13 | 14 |
| 4HS | 0.1 | 0.1 | 0.6 | 2.4 | 5.2 | 6.8 | 8.5 | 8.8 | 10 | 11 |
| 3XP | 0.1 | 0.1 | 1.0 | 3.4 | 6.0 | 7.1 | 12 | 12 | 20 | 23 |

In all the monkeys there was an increase in antibody titer (crossreacting with HIV-2). In immunized monkeys, antibody level decreased between day 28 and day 41 in 3X7, between day 41 and day 55 in 4GP, and between day 118 and day 146 in 4GI. In control monkeys, there is a progressive increase in antibody level. The decline in antibody level indicated again that in monkeys immunized by SIV-βgal, SIV is being eliminated.

The protection of vaccinated monkeys against infection was quite surprising in view of the fact that SIV-βgal did not induce neutralizing antibodies in vitro. This finding is consistent with the clinical observation that actively infected and ill AIDS patients have high levels of such neutralizing antibodies. The highly conserved antigenic sequences result in antibodies that are not neutralizing in vitro but are protective in vivo. Because the absolute level of antibody does not exhibit a straightforward correlation with protection against SIV infection, it is possible that cellular immune responses may be induced by these vaccine constructs and may play an important role in protection against SIV infection in vivo.

What is claimed is:

1. A fusion protein comprising:

an amino acid sequence selected from the group consisting of NVTENFNMWKN, KAKRRVVQREKRAVG, and EESQNQQEKNEQELLELDKWA; and a non-HIV polypeptide sequence, wherein said amino-acid sequence and said polypeptide sequence comprise the backbone of said fusion protein, wherein said fusion protein reacts with an HIV-positive serum.

2. A fusion protein as claimed in claim 1, wherein the amino acid sequence is NVTENFNMWKN.

3. A fusion protein as claimed in claim 1, wherein the amino acid sequence is KAKRRVVQREKRAVG.

4. A fusion protein as claimed in claim 1, wherein the amino acid sequence is EESQNQQEKNEQELLELDKWA.

5. A fusion protein as claimed in claim 1, wherein the non-HIV polypeptide sequence possesses an enzymatic property.

6. A fusion protein as claimed in claim 1, wherein the non-HIV polypeptide sequence is one to which most humans do not have any antibodies.

7. A fusion protein according to claim 1, wherein said amino acid sequence is joined via a peptide bond to an N-terminus of said non-HIV polypeptide sequence.

8. A fusion protein as claimed in claim 1, wherein the amino acid sequence is NVTENFNMWKN.

9. A fusion protein as claimed in claim 1, wherein the amino acid sequence is KAKRRVVQREKRAVG.

10. A fusion protein as claimed in claim 1, wherein the amino acid sequence is EESQNQQEKNEQELLELDKWA.

11. A fusion protein according to claim 7, wherein said non-HIV polypeptide sequence is β-galactosidase.

12. A fusion protein according to claim 1, wherein said non-HIV polypeptide sequence is β-galactosidase.

13. A fusion protein according to claim 1, wherein said amino acid sequence is one of NVTENFNMWKN and KAKRRVVQREKRAVG.

* * * * *